(12) United States Patent
Schmocker

(10) Patent No.: US 11,364,320 B2
(45) Date of Patent: Jun. 21, 2022

(54) CURABLE FILLER MATERIAL FOR TUBULAR STRUCTURES

(71) Applicant: ECOLE POLYTECHNIQUE FEDERALE DE LAUSANNE (EPFL), Lausanne (CH)

(72) Inventor: Andreas Schmocker, Lausanne (CH)

(73) Assignee: Ecole Polytechnique Federale de Lausanne (EPFL), Lausanne (CH)

( * ) Notice: Subject to any disclaimer, the term of this patent is extended or adjusted under 35 U.S.C. 154(b) by 61 days.

(21) Appl. No.: 16/315,901

(22) PCT Filed: Jul. 7, 2017

(86) PCT No.: PCT/IB2017/054099
§ 371 (c)(1),
(2) Date: Jan. 7, 2019

(87) PCT Pub. No.: WO2018/011680
PCT Pub. Date: Jan. 18, 2018

(65) Prior Publication Data
US 2019/0231921 A1    Aug. 1, 2019

(30) Foreign Application Priority Data

Jul. 11, 2016 (EP) .................................. 16178912

(51) Int. Cl.
*A61L 24/00* (2006.01)
(52) U.S. Cl.
CPC .......... *A61L 24/001* (2013.01); *A61L 24/0089* (2013.01); *A61L 2400/06* (2013.01); *A61L 2430/36* (2013.01)
(58) Field of Classification Search
CPC ............... A61L 24/001; A61L 24/0089; A61L 2400/06; A61L 2430/36
See application file for complete search history.

(56) References Cited

U.S. PATENT DOCUMENTS

| | | | | |
|---|---|---|---|---|
| 3,925,895 A | * | 12/1975 | Kliment | A61K 6/0038 433/224 |
| 7,186,761 B2 | * | 3/2007 | Soffiati | A61L 27/44 523/210 |
| 2004/0054413 A1 | * | 3/2004 | Higham | A61L 27/52 623/908 |
| 2005/0036946 A1 | * | 2/2005 | Pathak | A61P 17/04 424/9.4 |
| 2005/0043490 A1 | * | 2/2005 | Klee | A61K 6/20 525/285 |
| 2005/0089733 A1 | * | 4/2005 | Punsalan | H01M 4/8621 438/778 |
| 2005/0158272 A1 | * | 7/2005 | Whirley | A61P 35/00 424/78.18 |
| 2011/0053117 A1 | | 3/2011 | Engelbrecht et al. | |
| 2011/0070563 A1 | * | 3/2011 | Ori | A61K 6/54 433/224 |
| 2011/0230591 A1 | | 9/2011 | Berger | |
| 2012/0115982 A1 | * | 5/2012 | Klee | A61K 6/849 523/118 |
| 2014/0194733 A1 | * | 7/2014 | Goforth | B82Y 30/00 29/428 |

FOREIGN PATENT DOCUMENTS

| | | |
|---|---|---|
| EP | 1 547 571 | 6/2005 |
| EP | 2 452 667 | 5/2012 |

OTHER PUBLICATIONS

International Search Report for PCT/IB2017/054099, dated Oct. 26, 2017, 5 pages.
Written Opinion of the ISA for PCT/IB2017/054099, dated Oct. 26, 2017, 7 pages.

* cited by examiner

*Primary Examiner* — Jessica M Roswell
(74) *Attorney, Agent, or Firm* — Muncy, Geissler, Olds & Lowe, P.C.

(57) ABSTRACT

A radiopaque composition with low viscosity and increased photopolymerizability for application or filling of hollow structures is disclosed. Moreover, a method to apply and monitor the application and/or the photopolymerization of the composition are presented.

19 Claims, 5 Drawing Sheets

CURABLE FILLER MATERIAL FOR TUBULAR STRUCTURES

This application is the U.S. national phase of International Application No. PCT/IB2017/054099 filed 7 Jul. 2017, which designated the U.S. and claims priority to EP Patent Application No. 16178912.8 filed 11 Jul. 2016, the entire contents of each of which are hereby incorporated by reference.

TECHNICAL FIELD

The invention lies in the field of filler materials for biomedical applications.

BACKGROUND

Tissue fillers and material to replace soft and hard tissue such as bone or dental cements, liquid embolic agents or tissue sealants for different applications are usually injected or placed in a liquid, monomeric or pre-polymerized state and harden over time based on chemically or physically induced reactions, typically providing a poor control over the reaction by an operator. One option to actively control the polymerization is by using a photo-sensible material and a system for illumination to photopolymerize the injected material. As presented for instance in the International Patent Application WO 2016/038515, the optical light source used for polymerizing a filler material can also be used to obtain information about the injection process, the photopolymerization state of the material and/or the surrounding tissue before, during or after the photopolymerization. However, several technical challenges have to be overcome to efficiently illuminate the material/environment and to monitor such processes; particularly, in the case of topological complicated body structures such as tubular or branched ones, drastically different compared to substantially round cavities, such a monitoring process, but also the application of the material, results very challenging.

Several approaches have been proposed in the past, typically for dental root canal treatment such as obturation. For instance, US 2002/0176849 describes methods, devices and materials for the treatment or repair, replacement, transplantation or augmentation of tissues in endomural zones specifically by open surgical, minimally invasive or percutaneous transmural or trans-parenchymal application of polymeric material alone or in combination with bioactive agents or cells. These methods and systems are useful to repair, alter function, replace function or augment function of the central or endomural aspects of solid organs or tubular body structures.

U.S. Pat. No. 4,631,030 discloses an apparatus for putting light-hardening materials such as resins between teeth so to induce the polymerization of resin by light, starting from the approximal-apical zone of the tooth, i.e., at the base of the filling. It comprises a wedge transparent to the rays used and adapted to be inserted between the teeth, the wedge having means to refract or reflect concentrated light supplied to it in the axial direction by a light source, by deflecting it in the lateral direction, so as to illuminate the filing material with the greatest possible intensity in the approximal part of the cavity, enabling the hardening of the filling material starting from the approximal-apical stratum.

WO 2013/128952 describes a dental root canal treatment instrument equipped with an optical fiber bundle in which optical fibers are bundled, and a holding fixture that maintains the shape of the optical fiber bundle. The optical fiber bundle has a brush-like shape, and can include a photopolymerizable sealer. When the tip of the optical fiber bundle is inserted into a root canal and light is shone into the base end, the photopolymerizable sealer is hardened by the light emitted from the tips of the optical fibers, and the root canal treatment instrument is integrated with the root canal.

US 2009/0047634 describes a plug configured to be implanted into an endodontically prepared root canal of a tooth comprising an elongated body comprised of a biologically compatible, nonporous, material which is resilient after being chemically bonded to the inner surface of the root canal and an adhesive compound provided on a surface of said elongated body. The plug is positioned in a root canal and bonded to the root canal by applying a light-curing adhesive to the canal and exposing the plug to a light source to bond the plug to the root canal. In one embodiment, a filler material is heated and injected into the root canal in a semi-liquid state and exposed to light to cure the adhesive.

U.S. Pat. No. 9,023,917 describes an improved carrier composition for endodontic instruments useful for filling root canals comprising a cross-linkable material, particularly useful for retreatment of a root canal.

U.S. Pat. No. 5,503,559 relates to an endodontic apparatus and related method for preparing, sealing and restoring a tooth's root canal using induced fluorescence spectroscopy. A root canal probe having an optical fiber through its center transmits excitation light into the tooth's root canal. The excitation light induces the tissue within the root canal to fluoresce. The fluorescent light is collected by the optical fiber and transmitted back to a sensor that generates electrical signals indicative of the intensity of light within predetermined wavelength bands. The electrical signals are processed to identify the tissues within the root canal. Using the fluorescent emission properties of the tissues of components of a tooth, the entrance of the root canal is located. The root canal is cleaned and shaped and the apex of the root canal located using the difference between the fluorescence spectrum of the apex and the root canal. The root canal is sealed and filled by a light cure restorative delivered into the root canal through a tube. The light cure restorative is activated by light transmitted into the root canal by an optical fiber. The light activation and polymerization of the light cure restorative can be controlled by monitoring the intensity of the restorative's fluorescence spectrum.

All the above described prior art inventions present several drawbacks, notably related to the very peculiar morphology of anatomical tubular structures (particularly branched ones) and to the materials used. In fact, today's materials for use in applications related to the coating, replacement or filling of tubular body cavities are not intended for acting, at the same time, as functional matrices serving the aim they are designated for and as tools for monitoring the adequate application (e.g., injection) process and, in certain cases, the curing process. Moreover, the curing efficiency, which is directly related to the absorption and the scattering properties of a material, is insufficient in current products, especially when they require a low viscosity for injection and a high radiopacity for imaging.

Especially for tiny structures such as a dental root canal, the processes of the material application and monitoring thereof can be an uphill struggle. The dental root is composed by the pulp chamber (within the coronal part of the tooth), the main canal(s), and more intricate anatomical branches that may connect the root canals to each other or to the surface of the root. The total number of root canals per tooth depends on the number of the tooth roots ranging from one to four, five or more in some cases. Sometimes there is more than one root canal per root. Some teeth have a more variable internal anatomy than others.

The internal space of dental roots is often a complex system composed of a central area (root canals with round, oval or irregular cross-sectional shape) and lateral parts (fins, anastomoses and accessory canals). In fact, this lateral component may represent a relatively large volume, which challenges the cleaning phase of the instrumentation procedure in that tissue remnants of the vital or necrotic pulp as well as infectious elements are not easily removed in these areas. Thus, the image of root canals having a smooth, conical shape is generally too idealistic and underestimates the reach of root canal instrumentation.

The smaller branches, referred to as accessory canals, are most frequently found near the root end (apex), but may be encountered anywhere along the root length. An unusual root canal shape, complex branching (especially the existence of horizontal branches), and multiple root canals are considered as the main causes of root canal treatment failures; for example, if a secondary root canal goes unnoticed by the dentist and is not cleaned and sealed, it will remain infected, causing the root canal therapy to fail.

Current methods of obturating (filling) an extirpated (stripped) root canal commonly involve packing a root canal with a thermoplastic material, such as Gutta Percha (e.g., trans 1-4 polyisoprerie, Vectra™ or polysulfone), so that the root canal space is filled with the thermoplastic material. Preferably, the space is filled with the thermoplastic material forming a seal which prevents leakage between the root canal and the surrounding tissue.

Additionally, a sealer material may be added to improve the interface between the thermoplastic material and the tooth. However, these sealers are placed separately and may extrude into the region beyond the apex once the thermoplastic material is added on top. Another way to improve the interface between tooth and thermoplastic material is by heating up this latter.

To efficiently work, a material for use in root canal treatment must perfectly fit in every space of the root. To do so, it shall be efficiently injected in all branches, adequately adhere thereto, be visible upon X-ray scanning or tomography and possibly perfectly harden upon a curing process. In the reduction to practice, it is very difficult to comply with all these requirements, and they can eventually culminate in a poor final clinical result in terms of (re)establishment of a functional tissue, relapses of a pathological condition or even undesired secondary effects such as infections. There is therefore a need in the art for novel biomedical materials for overtaking the above-mentioned shortcomings.

SUMMARY OF INVENTION

Bearing in mind all the cited drawbacks of the currently available approaches, and in order to solve them, the present inventors developed a new biomaterial, as well as methods for using thereof, for filling a possibly branched tubular structure, as described herein and in the appended claims.

One aim of the present invention was to develop a material adapted to be reliably delivered into tiny (preferably in the range of 10 to 1000 μm in diameter) branched tubular structures as well as larger structures above 1 mm in diameters such as blood vessels or pulp chamber.

Another aim of the present invention was to develop a material with optimal characteristics in terms of high radio opacity and low viscosity as well as efficient photopolymerizability (low total attenuation coefficient at ultra-violet or visible wavelength) for being adequately delivered (i.e., injected), polymerized and monitored at the same time.

A further aim of the present invention was to identify the best features for solving the above-mentioned challenges and implementing them in a safe and biocompatible material useful in biomedical applications.

Still a further aim of the present invention was to develop a material adapted to be delivered in a user-friendly and patient-friendly, minimally-invasive way.

Finally, another aim was to combine the above material with a device and method to deliver and measure the amount of injected material, the distance between probe and proximal end of the tubular structure or a bifurcation within the tubular structure, or to measure, count and/or image the amount of bifurcations of the said tubular structure.

In particular, the developed biomaterial is especially, but not exclusively, intended to be used with an injection device, possibly in combination with a device adapted to photopolymerize a curable material, such as for instance the device disclosed in the International Patent Application WO 2016/038515, owned by the present Applicant and incorporated herein in its entirety by reference. The key technical challenge addressed by the present invention relied in the production of a suitable composition able to combine in one single product a low viscosity, a high radiopaque density and a low total attenuation coefficient at ultra-violet or visible wavelength, allowing to still photopolymerize the material.

In fact, a common problem observed in the available compositions for e.g. dental root treatment relies in the fact that, by including a radio opaque element in a carrier composition, this latter results hardly injectable through a syringe needle, such as 30 gauge needles intended for minimally invasive applications, due to an augmentation of the viscosity. Thus, a usually non-efficient balance of all other parameters of the composition must be put in place. On the other hand, looking for a good injectability of such compositions could result in a poor monitoring and/or photopolymerization outcome, particularly due to a non-efficient distribution in the target tubular (branched) cavities of the composition.

Accordingly, it is an object of the present invention to provide for a liquid or semi-solid composition for use as a filling agent for hollow structures comprising a liquid carrier; a cross-linkable polymeric material; a cross-linking agent; and a radiopaque agent, characterized in that it has i) an opaque density of at least 3 mmAl/mm, ideally at least 6 mmAl/mm, opaque density meaning amount of X-rays absorbed by millimetre of material compared to a 1-milimeter wedge of aluminium (e.g. 6 mmAl/mm means that 1 mm of material has the same radiopaque thickness/same X-ray absorption as a 6-milimeter-thick aluminium wedge) and ii) a viscosity comprised between $2 \times 10^{-4}$ and $1 \times 10^3$ Pa*s.

In one embodiment, the liquid carrier comprises a cross-linkable material that has an optical density resulting in an absorption coefficient of less than 1000 cm$^{-1}$ at a wavelength between 350 and 600 nm. Said absorption coefficient may be the total absorption coefficient or the material absorption coefficient excluding scattering contributions.

In one embodiment, the cross-linkable material is present in an amount comprised between about 0.5 g and about 40 g per 100 ml of composition, preferably between about 5 g and about 15 g per 100 ml of composition, more preferably about 10 g per 100 ml of composition. In a preferred embodiment, the cross-linkable material comprises a thermoset material. In one embodiment, the carrier is formulated as a hydrogel.

In one embodiment, the cross-linking agent is a photoinitiator. It may be present in an amount of at least about 0.001%, and preferably at least about 0.05% by weight of the composition. Furthermore, the curing agent may be present in an amount of less than about 15%, and preferably less than about 5% by weight of the composition. For example, the curing agent may be present in a range from about 0.001% to about 15%, and preferably from about 0.05% to about 5% e.g., about 0.1% to about 1%) by weight of the composition.

In one embodiment, the composition further comprises a co-initiator which is present in a molar ratio with respect to a photoinitiator (photoinitiator/co-initiator) comprised between about 100:1 and about 1:100, preferably between about 1:1 and about 1:10.

In one embodiment, the radio opaque material comprises one or several types of radiopaque atoms or molecules thereof. In one embodiment, the radio opaque material is present in an amount comprised between about 1 g to about 200 g per 100 ml composition. In a preferred embodiment, the radio opaque material is present in an amount comprised between about 60 g and about 90 g per 100 ml of composition.

In preferred embodiments, the radio opaque material comprises a non-metallic radiopaque atom. In another preferred embodiment, the radio opaque material comprises one or several metal atoms. In yet another preferred embodiment, the radiopaque material is a combination of a radiopaque material with non-metallic radiopaque atom(s) and radiopaque material with metallic radiopaque atom(s). In still a preferred embodiments, the radio opaque material comprises a mixture of Iodine-based material (including Iodine itself) and a metal-based material (including a metal itself), salt thereof and/or oxide thereof. In preferred embodiments, the metal-based material, salt thereof or oxide thereof is selected from a non-exhaustive list comprising barium sulphate, zirconium oxide, zinc oxide, calcium tungstate, gold, gadolinium, silver, platinum, tantalum as well as combinations of the foregoing. In one embodiment, the ratio between the Iodine-based material and other radio opaque materials is comprised between about 2:1 to 1:2 by weight.

In one embodiment, the hollow structures have a diameter comprised between 10 µm and 20 mm, preferably between 50 µm and 1000 µm. In one embodiment, the tubular structures or cavities are dental root canals and accessory canals, pulp chamber, blood vessels, aneurysms, lymphatic vessels, bronchi and bronchioles and natural or artificially-created tubular structures.

DESCRIPTION OF EMBODIMENTS

Figure 1:
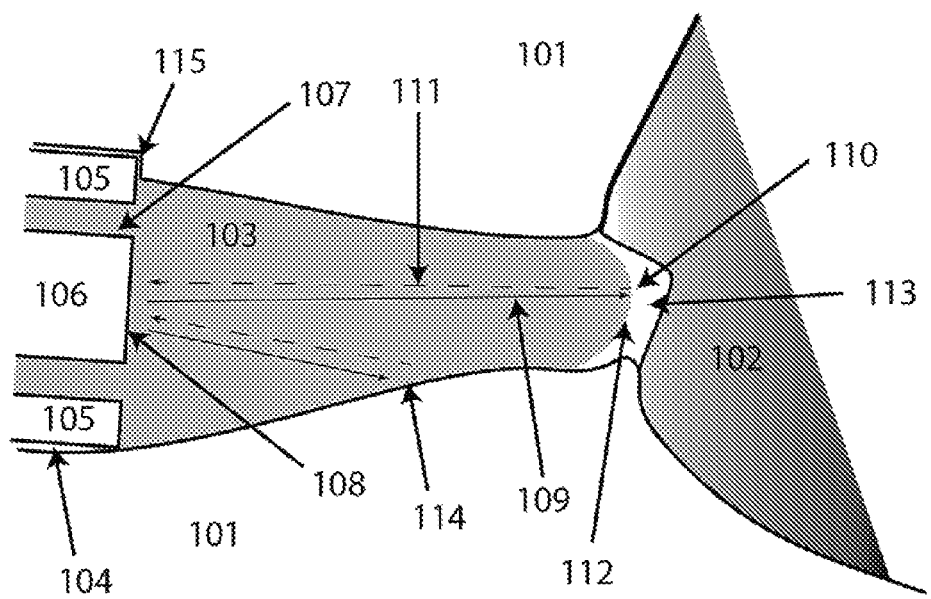
FIG. 1 depicts a probe placed within an tubular structure for photoinitiation, material delivery and monitoring.

The present disclosure may be more readily understood by reference to the following detailed description presented in connection with the accompanying drawing figures, which form a part of this disclosure. It is to be understood that this disclosure is not limited to the specific conditions or parameters described and/or shown herein, and that the terminology used herein is for the purpose of describing particular embodiments by way of example only and is not intended to be limiting of the claimed disclosure.

As used herein and in the appended claims, the singular forms "a", "an" and "the" include plural referents unless the context clearly dictates otherwise. Thus, for example, reference to "a tubular structure" includes a plurality of such structures.

Also, the use of "or" means "and/or" unless otherwise stated. Similarly, "comprise", "comprises", "comprising", "include", "includes" and "including" are interchangeable and not intended to be limiting. It is to be further understood that where descriptions of various embodiments use the term "comprising", those skilled in the art would understand that in some specific instances, an embodiment can be alternatively described using language "consisting essentially of" or "consisting of".

The invention will be better understood with the help of the following definitions.

In the frame of the present disclosure, the term "composition" is used interchangeably with the term "formulation". A "composition", as used herein, refers to a mixture of ingredients or compounds prepared in a certain way and used for a specific purpose. The concept is also clearly linked to the process in which different compounds are combined to produce a final product. Usually, since the ingredients impart peculiar properties to the final product (i.e., the final composition) when it is put into use, said ingredients are mixed according to a specific formula in order to obtain characteristic features for the final composition, such as e.g. the achievement of effects that cannot be obtained from its components when these are used singly, a higher degree of effectiveness to facilitate any potential synergistic action of their components, to improve handling or imaging properties and/or safety for end user and the like.

The compositions of this invention may be in a variety of forms, the preferred one usually depending on the intended mode of administration and/or intended application. In a preferred embodiment, the composition is formulated into an injectable form. If required, the composition can be further mixed with an amount of water or physiologically compatible buffer sufficient to produce the desired consistency for injection. Preferable compositions according to the invention should be able to pass through a 30 gauge needle syringe. Other gauged syringes may also be used such as a 32-28-25-18-16-14 or 12 gauge syringes or syringes with thickness in-between or above, as well as larger structures such as catheters or cannulas. The ability to flow through small-gauged needles is preferred in the frame of the applications envisaged for the composition of the invention, notably for the use of the said composition for a minimally-invasive treatment on a subject. Moreover, any type of geometry may be used such as for example double-cylindrical (flow within an inner and an outer cylinder), conic or rectangular volume instead of a tubular or cylindrical volume.

Compositions normally comprise at least one acceptable carrier for the compounds comprised in the formulation (and which can also serve, in case, as a diluent means), excipients and so forth. As used herein, a "carrier" is any substance which functions as a dispersing mean for the elements of the composition of the invention, particularly for the cross-linkable polymeric material, and which allows a suitable delivery thereof. The term includes any and all solvents, liquid diluting agents, absorption delaying agents and the like, that are physiologically compatible with the end user. Examples of suitable carriers are well known in the art and include aqueous solutions (e.g. sodium chloride solutions, phosphate buffered sodium chloride solutions and the like), water, oils, emulsions such as oil/water emulsions, various types of wetting agents, gels, hydrogels and so forth. In some preferred embodiments of the invention, the carrier is a liquid carrier, preferably an aqueous solution, including water.

A composition according to the present disclosure can be provided in liquid form. A liquid composition is a composition in which the carrier is a liquid carrier and which maintain a liquid or viscous form notwithstanding the presence of any another added excipient. A liquid formulation includes e.g. aqueous solutions, non-polar solutions or emulsions. An "aqueous solution" is a solution in which the solvent is substantially made of water. In the frame of the present disclosure, the term "aqueous" means pertaining to, related to, similar to, or dissolved in water. The expression also includes highly concentrated and/or viscous solutions, in which the water content is e.g. less than 5% in weight of the total solution. A "non-polar solution" is a solution in which the solvent is a non-polar compound. Non-polar solvents are intended to be compounds having low dielectric constants and that are not miscible with water. Non-polar solutions can comprise for example oils. An "oil" is any non-polar chemical substance that is a viscous liquid at ambient temperatures and is both hydrophobic and lipophilic. An "emulsion" is a mixture of two or more fluids that are normally immiscible (unblendable). Emulsions are part of a more general class of systems of matter called colloids. Although the terms colloid and emulsion are sometimes used interchangeably, in the frame of the present disclosure the term emulsion is used when both the dispersed and the continuous phase are fluids, such as e.g. liquids. In an emulsion, one fluid (the "dispersed phase") is dispersed in the other (the "continuous phase").

In some embodiments, a composition according to the present disclosure can be provided in a semi-solid form, such as in case of gels or hydrogels. As used herein, the term "gel" refers to a non-fluid colloidal network or polymer network that is expanded throughout its whole volume by a fluid. A gel is a semi solid three-dimensional network that spans the volume of a liquid medium and ensnares it through surface tension effects. It is a soft material, that is, it is compressible, malleable, ductile and/or plastic, and can comprise or consist of a polymeric matrix, i.e. and organised or amorphous network of monomeric elements. The internal network structure may result from physical bonds (physical gels) or chemical bonds (chemical gels).

As used herein, the term "hydrogel" refers to a gel in which the swelling agent is an aqueous solution. A hydrogel is a macromolecular polymer gel constructed of a network of crosslinked polymer chains. It is synthesized from hydrophilic monomers, sometimes found as a colloidal gel in which water is the dispersion medium. Hydrogels are highly absorbent (they can contain over 90% of an aqueous solution) natural or synthetic polymeric networks. As a result of their characteristics, hydrogels develop typical firm yet elastic mechanical properties with elastic moduli between some Pa and several MPa, ultimate strength ranging up to several tens or hundreds of MPa and deformations may range up to several thousand folds.

The composition of the present invention is characterized by a viscosity before polymerization comprised between $2\times10^{-4}$ and $1\times10^3$ Pa*s. Ideally, said viscosity is comprised between about $10^{-2}$ Pa*s and about 10 Pa*s. The inventor has been able to identify such viscosity values as the optimal ones in view of the provision to deliver the composition 1) through injection means, preferably via small-gauged needles 2) within thin bodily tubular structures or cavities and 3) preferably in a pressurized way, as will be detailed later on.

The cross-linkable polymeric material to be used may comprise in some embodiments one or more compounds selected from a non-exhaustive list comprising natural polymeric materials (i.e., non-synthetic polymers, polymers that can be found in nature) and/or polymers derived from the Extra Cellular Matrix (ECM) as gelatin, elastin, collagen, agar/agarose, chitosan, fibrin, proteoglycans; a polyamino-acid or its derivatives, preferably polylysin or gelatin methyl cellulose, carbomethyl cellulose, polysaccharides and their derivatives, preferably glycosaminoglycanes such as hyaluronic acid, chondroitinsulfate, dermatansulfate, heparansulfate, heparine, keratansulfate or alginate, nucleotides, polylipides, fatty acids, poly lactic acid, lactic acid, as well as any derivative thereof, fragment thereof and any combination thereof.

The polymeric material can also comprise one or several synthetic or semi-synthetic biodegradable materials. Depending on the degradation rate of the material, cells can migrate into it and possibly replace it. Examples of such materials are hydroxyapatite, poly(lactic-co-glycolic acid), lactide and glycolide polymers, caprolactone polymers, hydroxybutyric acid, polyanhydrides, polyesters, polyphosphazenes, polyphosphoesters, polycaprolactone (PCL) or a combination of PCL, caprolactone, ureido-pyrimidinone, bisurea and poly(glycerol sebacate acrylate).

In one embodiment, the composition comprises an antibacterial or anti-fungal material such as cephalosporins, penicillin, aminoglycoside, gentamicin, vancomycin or undecylenic acid, an antimicrobial peptide or other antibacterial material such as poly(D,l-lactide) (PDLLA), silver nano particles, chitlac or microspheres prepared with encapsulated silver nanoparticles.

In preferred embodiments according to the present invention, the cross-linkable polymeric material is a thermoset material (e.g., rubbers and/or plastics). A "thermoset" is a pre-polymer in a soft solid or viscous state that changes irreversibly into an infusible, insoluble polymer network by curing. Curing is induced by the action of heat or suitable radiation, often under high pressure. The curing process transforms the resin into a plastic or rubber by cross-linking individual chains of the polymer. The cross-linking is facilitated by energy and catalysts at chemically active sites, which may be unsaturated sites or epoxy sites, for example, linking into a rigid, three-dimensional structure. This yields molecules with a large molecular weight, resulting in a material that usually decomposes before melting. Therefore, a thermoset cannot be melted and re-shaped after it is cured.

Examples of thermoset materials include, but are not limited to, alkyds, epoxies, phenolics (e.g., Bakelite), polyimides, formaldehyde resins (e.g., urea formaldehyde or melamine formaldehyde), polyester thermosets, unsaturated polyesters, polyurethane, bis-maleimides (BMI), silicone materials such as polydimethylsiloxane (PDMS) and any combination thereof.

Further suitable materials according to the present invention may comprise one or more compounds selected from a non-exhaustive list comprising polypropylene, polypropylenoxide or their derivatives, polymethylenoxide or its derivatives, polyethylene or its derivatives such as polyethylene glycole (PEG), polyethylenoxide or their derivatives, polyacrylate or its derivatives, poly(vinyl alcohol) (PVA) and copolymers, poly(vinylpyrrolidone) (PVP) and combinations thereof.

Several physical properties of the (hydro)gels are dependent upon concentration. Increase in (hydro)gel concentration may change its pore radius, morphology, or its permeability to different molecules. One skilled in the art will appreciate that the volume or dimensions (length, width, and thickness) of a (hydro)gel can be selected based on instant needs, such as for instance the region or environment into which the (hydro)gel is to be implanted or such as whether it has to biodegradable or not, or such as whether cells or bacteria should migrate inside or not.

The mechanical properties of the material can be tailored according to said needs by changing the physical or chemical properties thereof (molecular chain length, crosslinking rate, water content and so forth). In this context, in order to optimize the mechanical properties of the composition of the invention, it is contemplated a polymer density comprised between 0.5 and 90 g per 100 mL, which is considered to be a suitable density for the carrier material according to the invention. In preferred embodiments, the cross-linkable material is present in an amount comprised between about 0.5 g and about 40 g per 100 ml of composition, preferably between about 5 g and about 15 g per 100 ml of composition, more preferably in an amount of about 10 g per 100 ml of composition.

In most preferred embodiments, the polymeric carrier material is not crosslinked or minimally crosslinked in order to keep the composition in a suitable needle-injectable form. If needed, crosslinking agents and their amount can be chosen at the operator's discretion, and a skilled in the art would easily envisage such parameters based on common practice. With the aim of favouring the polymerization of the composition, in one preferred embodiment methacrylate groups, diacrylate groups or the like are coupled to the polymeric cross-linkable material present in the carrier. Any other molecule or end group attached to the carrier and enabling the polymerization or crosslinking of the carrier may be used.

Polymeric materials can be mixed with inorganic particles (usually in the form of continuous fibres, such as glass or particulates such as mica, talc and clay) in order to modify and improve (mainly but not exclusively) their mechanical properties. Reinforcement using organic fibres (for example, kevlar (poly(paraphenylene terephthalamide), cellulose fibers or carbon fibres) is also possible.

In one particular embodiment, a hydrogel composite material comprising polyethylene glycol dimetacrylate and cellulose fibers can be used as a carrier.

In some embodiments of the invention, the cross-linkable material is a hydrophilic cross-linkable polymeric material, such as e.g. natural polymeric materials and/or polymers derived from the extracellular matrix, having such a polymer concentration and chain length to induce a high osmotic pressure, after photopolymerization, within the tubular structures or cavities it is disposed in, in such a way that the obtained pressure exerts a force onto the walls of the tubular structures to seal them. One preferred aspect related to these embodiments is that of obtaining a composition having such properties to mimic the properties of extracellular matrix in terms of elastic modulus, porosity, swelling, water content, osmotic pressure, equilibrium modulus, ultimate compressive or tensile strength and/or biomolecular aspects characterizing a given tissue.

In one embodiment, the concentration of the hydrophilic cross-linkable polymeric material is comprised between 0.01 and 95% weight per volume of composition, preferably between 5 and 30% weight per volume of composition.

In one embodiment, the composition comprising a hydrophilic cross-linkable polymeric material has an elastic modulus comprised between 1 Pa and 1 GPa, preferably between 1 and 1000 kPa. The ultimate compressive or tensile strength of the material is at least 10 GPa, preferably at least 100 MPa or even more preferably at least 1 MPa.

In one embodiment, the chain length of the hydrophilic cross-linkable polymeric material ranges from about 1 Da to about 500 kDa, preferably between 700 Da and 25 kDa. The osmotic pressure obtainable limits the migration of material or fluids such as bacteria, blood or body fluids through the tubular structure or cavity resulting in the said sealing or blocking effect. The sealing or blocking is achieved by an external force induced by the osmotic pressure inside the material. This force is directed towards the cavity wall and seals interspaces between said polymeric material and the cavity wall. As a result of the above-mentioned structural/mechanical features of the polymeric material, as well as of its amount, the resulting osmotic pressure (or internal pressure) is typically comprised between 100 Pa and 50 MPa, and is preferably comprised between 50 kPa and 10 MPa.

The above-mentioned aspects of the composition of the invention are particularly useful when the said composition is intended for use in the treatment of the dental pulp through pulpotomy, a technique characterized by the complete or partial removal of coronal portion of pulp followed by placement of medicament, with the intent of maintaining the vitality of the remaining pulpal tissue by means of a therapeutic dressing. A healthy tooth has a space inside it called the "pulp space" which is filled with soft tissues—nerves, blood vessels, and connective tissue. If a tooth gets a large cavity, the bacteria in the decay can damage the pulp, which is often what causes toothache. Currently, Zinc Oxide, Glutaraldehyde and Ferric sulfate are used as part of the treatment; however, the major disadvantages of these materials are their toxicity, inflammation after implantation, insufficient adhesion or tissue integration to surrounding tissue, the missing ability to adapt during the growth of the teeth and, in case of partial pulpotomy, the tissue integration and mimicking of the native pulp tissue. These issues could be solved by using a swellable, biocompatible, native-tissue-mimicking and resistant hydrogel-based material according to the invention.

In one preferred embodiment, the composition includes a material to reinforce surface adhesion. This could be dispersed particles (e.g. $SiO_2$ such as LUDOX® TM-40 colloidal silica from Sigma Aldrich), a fibrous material such as those previously mentioned and/or any other suitable material which fosters interlocking, diffusion, crosslinking or adhesion to a neighboring element, such as a surface of a tubular structure.

In order to be hardened once or while injected into tubular structures, the composition of the invention further comprises a cross-linking agent, also referred herein as "curing agent". It is appreciated that the curing agent may be employed to chemically cross link the cross-linkable (e.g. thermoset) material. Suitable crosslinking agents can comprise for instance 1,4-Cyclohexanedimethanol divinyl ether, di(ethylene glycol) diacrylate, di(ethylene glycol) dimethacrylate, polyacrylamaide, N,N'-(1,2-Dihydroxyethylene) bisacrylamide, divinylbenzene, p-Divinylbenzene, ethylene glycol diacrylate, ethylene glycol dimethacrylat, 1,6-Hexanediol diacrylate, 4,4'-M ethylenebis(cyclohexyl isocyanate), 1,4-Phenylenediacryloyl chloride, poly(ethylene glycol) diacrylate, poly(ethylene glycol) dimethacrylate, tetra(ethylene glycol) diacrylate or tetraethylene glycol dimethyl ether.

In a preferred embodiment, the curing agent is a photoinitiator. A "photoinitiator" is a molecule that creates reactive species (free radicals, cations or anions) when exposed to an electromagnetic radiation such as UV or visible light. Example of suitable visible or ultraviolet light-activated photoinitiator includes ITX 4-Isopropyl-9-thioxanthenone, Lucirin TPO 2,4,6-Trimethylbenzoyl-diphenyl-phosphineoxide, Irgacure 184 1-Hydroxy-cyclohexyl-phenyl-ketone, Irgacure 2959 1-[4-(2-Hydroxyethoxy)-phenyl]-2-hydroxy-2-methyl-1-propane-1-one, Irgacure 819 Phosphine oxide, phenyl bis (2,4,6-trimethyl benzoyl), LAP lithium phenyl-2,4,6-trimethylbenzoylphosphinate, Riboflavin 7,8-dimethyl-10-((2R,3R,4S)-2,3,4,5-tetrahydroxypentyl) benzo [g] pteridine-2,4 (3H, 10H)-dione, Rose Bengal 4,5,6,7-tetrachloro-2',4',5',7'-tetraiodofluorescein, PL-BDK Benzil dimethyl ketal, PL-CPK 1-hydroxy-cyclohexylphenyl-ketone, PL-HM PP 2-hydroxy-2-methyl-1-phenyl-1-propanone, Camphorquinone, 3-(4-Quantucure BPQ benzoylphenoxy)-2-hydroxy-N,N,N-trimethyl-1-propanaminium-chloride, APi-180 hydroxyalkylpropanone, bisacylphosphineoxide- or monoacylphosphineoxide-based initiators. In a preferred embodiment, a bis(acyl)phosphineoxide-derived (BAPO) photoinitiator such as bis(1,3,5-trimethylbenzoyl)phosphinic acid (BAPO-OH) is used. Other examples of suitable BAPO photoinitiators are given in the following references such as: K. Dietliker, A compilation of photoinitiators commercially available for UV today, SITA Technology Ltd, Edinbergh, London, 2002; J. V. Crivello, K. Dietliker, G. Bradley, Photoinitiators for free radical cationic & anionic photopolymerisation, John Wiley & Sons, Chichester, West Sussex, England, New York, 1998; S. Benedikt, J. Wang, M. Markovic, N. Moszner, K. Dietliker, A. Ovsianikov, H. Grützmacher, R. Liska, J. Polym. Sci., Part A: Polym. Chem. 2016, 54, 473-479; T. Majima, W. Schnabel, W. Weber, Makromol. Chem. 1991, 192, 2307-2315; S. Li, F. Wu, M. Li, E. Wang, Polymer 2005, 46, 11934-11939; M. A. Tasdelen, B. Karagoz, N. Bicak, Y. Yagci, Polymer Bulletin 2008, 59, 759-766; B. D. Fairbanks, M. P. Schwartz, C. N. Bowman, K. S. Anseth, Biomaterials 2009, 30, 6702-6707; A. Huber, A. Kuschel, T. Ott, G. Santiso-Quinones, D. Stein, J. Bräuer, R. Kissner, F. Krumeich, H. Schönberg, J. Levalois-Grützmacher, H. Grützmacher, Angew. Chem. 2012, 124, 4726-4730; G. Müller, M. Zalibera, G. Gescheidt, A. Rosenthal, G. Santiso-Quinones, K. Dietliker, H. Grützmacher, Macromol. Rapid Commun. 2015, 36, 553-557.

The curing agent (e.g., photoinitiator) may be present in an amount of at least about 0.001%, and preferably at least about 0.05% by weight of the composition. Furthermore, the curing agent may be present in an amount of less than about 15%, and preferably less than about 5% by weight of the composition. For example, the curing agent may be present in a range from about 0.001% to about 15%, and preferably from about 0.05% to about 5% e.g., about 0.1% to about 1%) by weight of the composition.

In certain cases a co-initiator such as amines will be used (e.g. Triethylamine) or any other compound known in the art to be used as a co-initiator during photopolymerization. Preferably, a co-initiator is present in a molar ratio with respect to a photoinitiator (photoinitiator/co-initiator) comprised between 100:1 and 1:100, preferably between 1:1 and 1:10.

A special feature of the composition of the invention relies in the presence of a radio opaque material. It will be appreciated that a "radio opaque material" is a material that contributes to at least the 70%, preferably to at least the 90%, the radiopacity of the composition of the present invention. In most cases, said radio opaque materials are atoms or compounds comprising atoms having the highest atomic weight within the molecule, the compound or the material (in case several said radiopaque materials the second highest and so forth). In the frame of the present disclosure, the term "radiocontrast agent" can be interchangeably used to indicate radio opaque material. A general definition of a radiocontrast agent is a type of medical contrast medium used to improve the visibility of internal bodily structures in X-ray-based imaging techniques such as computed tomography (CT), radiography, and fluoroscopy. In another embodiment, contrast agents for other imagine techniques such as magnetic resonance imaging (MRI) are used.

The radio opaque material may be present in an amount of at least about 1 g per 100 ml of composition, and preferably at least about 10 g per 100 ml of composition. Furthermore, the radio opaque material may be present in an amount of less than about 200 g per 100 ml of composition, and preferably less than about 150 g per 100 ml of composition. For example, the radio opaque material may be present in a range from about 1 g to about 150 g per 100 ml of composition, and preferably from about 10 g to about 150 g per 100 ml of composition (e.g., between about 60 g and about 90 g per 100 ml of composition). In one embodiment, the radio opaque material comprises a metal, e.g. the radio opaque material may consist of or comprise metal or met-alloid molecules, oxides and/or salts thereof. Examples of metal or metal-based radio opaque materials can be selected from a non-exhaustive list comprising barium sulphate, zirconium oxide, zinc oxide, calcium tungstate, gold, gadolinium, silver, platinum, tantalum as well as combinations of the foregoing or derivations thereof. Such derivation may include any type of molecular or atomic structure surrounding them or attached to them. Such structure can give an extended range or material properties to the radiopaque material such as hydrophobicity, hydrophilicity, solubility (in water or any other solvent), biocompatibility and so on.

In preferred embodiments, the radio opaque material comprises Iodine or Iodine-based materials. Examples for commercially available Iodine based contrast agent are Cystografin, DaTscan, Isovue or diatrizoate. In still preferred embodiments, the radio opaque material comprises a mixture of Iodine (including Iodine-based materials) and a metal or a metal-based material, salt thereof and/or an oxide thereof as the ones previously listed. In one preferred embodiment, the ratio between Iodine and other radio opaque materials is comprised between about 2:1 to 1:2 by weight. The radio opaque material may be provided in the form of particles having an average particle size of e.g. between about 0.25 microns to about 10 microns, such as for instance between about 1.25 microns to about 2 microns. Suitable examples of radio opaque materials combinations and their ratios are provided in Table 1.

| Sample # | Formulation | Radiopaque density [mmAl/mm] |
|---|---|---|
| 1 | Zirconium oxide 5 mg/ml | Out of range |
| 2 | Zirconium oxide 25 mg/ml | 0.5 |
| 3 | Zinc oxide 5 mg/ml | Out of range |
| 4 | Zinc oxyde 25 mg/ml | Low homogeneity/no photopolymerization |
| 5 | Calcium Tungsten 5 mg/ml | Out of range |
| 6 | Ca Tungsten 25 mg/ml | 1.5 |
| 7 | Barium sulfate 5 mg/ml | Out of range |
| 8 | Barium sulfate 25 mg/ml | Low homogeneity/no photopolymerization |
| 9 | Gold particles 5 mg/ml | Out of range |
| 10 | Gold particles 25 mg/ml | 1.25 |
| 11 | Platinum particles 5 mg/ml | Low homogeneity/no photopolymerization |
| 12 | Platinum particles 25 mg/ml | Low homogeneity/no photopolymerization |
| 13 | Iodine 370 mg/ml | 3.75 |
| 14 | Saturated Iodine (>370 mg/ml) | 4 |
| 15 | Iodine 370 mg/ml + Calcium Tungstate 500 mg/ml (average of 2 samples) | 6.75 |
| 16 | Iodine 370 mg/ml + Calcium Tungstate 500 mg/ml (average of 3 samples) | 6.8 |
| 17 | Iodine 370 mg/ml + Zirconium oxide 500 mg/ml | Low homogeneity/no photopolymerization |

In a preferred embodiment, optically transparent cross-linkable materials are dispersed in an aqueous solution carrier, which allows creating a highly radiopaque and at the same time highly transparent final composition, wherein highly radiopaque means that the radiopacity of 1 mm thick composition corresponds to at least the radiopacity of 3 mm of aluminum, or even 6 mm of aluminum, and wherein highly transparent means that through a 1 cm thick sample at least 1% or 10% of visible light is transmitted, preferably 50%, even more preferably 95% or 99.9%.

A person skilled in the art will appreciate that the radiopacity described in mm of aluminum per mm of composition can also be described using other radiopacity units such as, but not limited to, Houndsfield units as well as other descriptions of absorption such as measuring the absorption cross-section (e.g. in barns/atom), using the mass absorption coefficient of a material or a probability of absorption or scattering per length, volume or mass.

In the production process of the composition of the invention, for instance two powder-based radiopaque materials may be mixed to an aqueous carrier comprising a cross-linkable material. Alternatively, a liquid solution comprising a radiopaque material may be used as carrier, to which the polymer and e.g. other radiopaque markers are added. The challenge in designing such a material is the high amount of radiopaque material within a solution; in fact, on one side the radiopaque materials usually significantly increase the viscosity of the composition and strongly absorb light (electromagnetic radiation), which significantly reduces the photopolymerization speed or limits the photopolymerization to a limited volume around the light source, e.g. only a part of the tubular structure close to the light source. The materials provided in the present invention and their relative amounts allows the final composition to be still injectable through a 32, 30, 28, 25 or 18 gauge needle (inner diameter of 108 μm or more), even after addition of the radiopaque metal materials to e.g. a hydrogel carrier. Furthermore, the composition can still be photopolymerized (with at least 70, preferably at least 90 of conversion rate) up to a depth of 3 cm within a tubular structure in less than 2 minutes (see FIG. 5, sample in the middle).

The composition may include one or more optional additives. The additives may include an antimicrobial (e.g., zinc oxide or silver nanoparticles), antibiotics, active agents with therapeutic effects, disinfection solutions, scattering additives for increasing the efficiency of the photopolymerization, softening agents, humectants, lubricants or any combination thereof. Said additives can be used for instance for anti-bacterial prolonged effect and/or antibiotic immediate effect. In some embodiments, an active agent may diffuse over time to counter or avoid infections. Additives may be useful for instance in the case of a root canal treatment where the most common cause of failure is a re-infection due to remaining bacteria within the root cannel cavity or bacteria migration back into the cannel from outside. In some embodiments, scattering additives which can increase the efficiency of the photopolymerization, having a scattering coefficient in suspension comprised preferably between 0.001 to 1000 $cm^{-1}$, may be envisaged in the composition. Such additives may be for example lipid particles, fibrous particles such as fibrillated cellulose, any of the radiopaque materials mentioned previously or other compounds complying with the scattering coefficient previously mentioned or known in the art.

The additive may be present in an amount of at least about 0.001%, and preferably at least about 0.01% by weight of the composition. Furthermore, the additive may be present in an amount of less than about 50%, and preferably less than about 25% by weight of the composition. For example, the additive may be present in a range from about 0.001% to about 50%, and preferably from about 0.01% to about 25% (e.g., about 0.05% to about 10%) by weight of the composition.

In one embodiment, the photoinitiator molecules are placed in the tubular cavities before filling the cavity with the photosensitive material. The photoinitator molecules are suspended in a solvent such as water, PBS, a polar or non-polar, protic or aprotic solvent. The solvent properties, such as its hydrophilicity, enhance the diffusion of the solution close to proteins, lipids and other biological molecules, into small cavities or parts of the tubular structure containing such molecules or aggregations thereof. The photoinitator placed close to these molecules will create radicals upon illumination react with the molecules. As for the photosensitive material, a set of possible photoinitiators can be used for the photoinitiator solution. Upon illumination the radicals destroy at least 50%, at least 90%, at least 99%, at least 99.9%, at least 99.99% or at least 100% of the said molecules in less than 5 seconds, less than 30s seconds, less than 1 minute or less than 5 minutes.

In one embodiment, the composition is used as an antibacterial treatment, to disinfect the structure, remove fungi, kill viruses or other microorganisms. The radicals induce oxidative stress which leads to the destruction of bacteria, fungi or other microorganism. The properties of the solvent, its viscosity, surface tension and hydrophilicity allow diffuse close to or penetrate into aggregations of several microorganisms, such as bacterial films. Thus the photoinitiator molecules a brought close to the microorganism and upon illumination can destroy at least 50%, at least 90%, at least 99%, at least 99.9%, at least 99.99% or at least 100% of the microorganism in less than 5 seconds, less than 30s seconds, less than 1 minute or less than 5 minutes.

As it will be therefore evident, in a preferred embodiment the photosensitive molecule within the photosensitive material is used at the same time for crosslinking and antibacterial and/or anti-fungal treatment.

In one embodiment the composition is tuned to have a hydrophilicity, measured using the dynamic contact angle method, with a contact angle between −30° and 100°, −25° and 50° or even between −20° and 10°. Such a hydrophilicity allows the composition to flow into millimetre-sized, micrometre-sized or even nanometer-sized interstices, wall irregularities, hollow spaces on the cavity wall or interspaces between elements situated on the wall such as colony of bacteria. It is understood that the hydrophilicity can also be expressed using for instance the transfer free energy (kcal/mol). Further information can be found in Jennissen, 2001, Biomaterials, 2, 45-53.

In a preferred embodiment the cavity walls are further treated with a liquid composition to change the surface tension of the walls which will further enhance the said flow into said interstices.

The tubular structures or cavities to be filled consist usually of canal s or cavities with a diameter smaller than 30 mm, typically smaller than 1 mm or even below 100 μm. Their length may vary between several tens or hundreds of millimeters and a few millimeters. Tubular structures are typically formed of one or several tubular elements which may be connected between each other. They may form branched structures with several bifurcations, but could also be independent tubes which are not connected. Typical examples for such structures are dental root canals and accessory canals, cavities in bones and teeth (e.g. the pulp chamber), blood vessels, aneurysms, lymphatic vessels or bronchi and bronchioles. They may be naturally present in a subject's body (e.g. the blood vessels of a cancer) or artificially created such as an access channel for surgery, a hole drilled into a tooth or into a bone, or combinations thereof or part extracted from an organ such as apicectomy or disectomy. Additionally, tubular structures can be completely artificial structures used for e.g. (biomedical) research purposes or surgical training.

The term "subject" as used herein refers to animals such as mammals, birds, insects and so forth. For example, mammals contemplated by the present invention include human, primates, domesticated animals such as cattle, sheep, pigs, horses, laboratory rodents and the like.

The tubular structures may have an open distal or proximal entry, and they can be open on one side and closed on the other or they can be completely closed on both sides. The same is the case for branched structures or tiny cavities, which may have one or several openings as well as none. To access the structure, an existing or artificially created opening may be used. They can also be accessed anywhere between the distal and the proximal end of the tubular or branched structure by piercing a hole into the lateral wall of one or several tubular elements.

Such an access is required to place a composition typically in liquid or semi-liquid formulation with a viscosity comprised preferably between about $2 \times 10^{-4}$ and about $1 \times 10^3$ Pa*s. To place the composition, a delivery system is required, typically consisting of injection mechanism or other delivering mechanisms such as stuffing, pressurization or pushing mechanism, described later on in more details.

One aspect of the present invention relates to the photo-activation (herein also referred to as "photopolymerization" or "photocuring") of the delivered composition within the above-described tubular structures. Moreover, the invention foresees the use of a method to distribute light in a linear or branched tubular structure, to pseudo-image the structure and/or determine the amount of branches, to block liquid flow within such a structure, and to determine the volume to be filled. For this, an illumination system combined within an injection device or separately brought close to it (i.e. in direct contact to, within or at a distance below 1 cm from the injected composition) can be used. Alternatively or additionally, delivery of a suitable electromagnetic radiation trough another material such as a bodily tissue is envisageable, as long as the delivered radiation is able to reach the injected composition. In a preferred embodiment, the illumination system consists of one or several light sources such as lamp, LED or laser source providing light typically in the wavelength range of 180 to 2000 nm, for instance in the range between 300 and 650 nm. Such a light, also referred to herein as "actinic light", is capable of starting and sustaining a photo chemical polymerization reaction of the composition upon injection thereof in a tubular structure. Basically, a composition according to the present disclosure is delivered (e.g. injected) in liquid or semi-solid form and then harden in situ by a photo chemical reaction. Upon illumination through an actinic light, the photons absorbed by the composition change the energy levels of electrons which then trigger the chemical reaction by creating free radicals, cations or anions which will induce the activation such as a solidification of the polymer.

In the case of bodily tubular structures or cavities of a subject, in order to place the composition of the invention in a minimally invasive way, it is preferable to access the target structures with a delivery system such as an injection device (e.g. thin gauged needles or a catheter). A light delivery system such as an optical fibre connected to a light source will ensure the selective illumination of the injected composition. Typically, the delivery device to place an injectable composition is smaller than 2 mm in diameter, preferably smaller than 800 μm and ideally smaller than 300 μm. An illumination device may be placed within the injection device or next to it, and it can have a diameter between several μm and several hundreds of μm.

In a preferred embodiment according to the invention, a device for these aims is the one described in International Patent Application WO 2016/038515, owned by the present Applicant and incorporated herein in its entirety by reference.

In one embodiment, there are other additional light sources for imaging, scanning or retrieving information from the injected material, the surrounding tubular element or any other artificially placed or existing structure outside or inside the tubular element, hereafter referred to as "illuminated element". The retrieved information may consist of data about the chemical structure, geometrical arrangement or structure, the liquid, semi-liquid or solid state of the illuminated element. The retrieved information may consist of a measured distance such as the distance between e.g. the probe tip of the illumination system and the injected composition, the distance between said probe tip and the illuminated composition and/or the distance between two illuminated elements. This latter possibility results particularly useful in case of branched tubular structures such as root canals, bronchiole, capillaries and the like.

The optical techniques to evaluate the retrieved information can be interferometry, Raman or fluorescence spectroscopy, imaging through a multimode or multicore fiber, or by an endoscope as well as X-ray tomography, fluoroscopy or X-ray scans performed from outside the tubular structure.

With reference to FIG. 1, a cross-section view of a tubular structure surrounded laterally by a body 101 and at the distal end by a body 102 is shown. 101 and 102 may, but do not need to consist of the same physical structure and/or material. The composition 103 is delivered into the tubular element using an injection channel 105. The composition 103 may fill the entire tubular element or also leave free spaces such as 113 and 104. In one preferred embodiment, free spaces 104 and/or 113 are also filled with the composition or with any other liquid or solid material such as for instance water, phosphate buffer solution or DMSO. An illumination and light transport element 106 with a surface (108) where light is emitted or collected is used to deliver electromagnetic radiation 109 to the composition 103, the surrounding bodies 102 and 101, to the empty spaces 113 and 104, and to the interfaces (110, 114) between said materials and/or bodies and/or empty spaces. Radiation 111 transmitted back to the body 106 contains information regarding the chemical composition, the material state (liquid, solid, gas), the temperature, the velocity, the refractive index or any other type of information describing a material or an interface between materials. As mentioned previously, this information also may consist of a distance measurement between any of said elements. Therefore, the system may also include a stopping mechanism, herein illustrated as mechanical blocking element (115). This may be a shape previously punched, drilled or otherwise made into the tubular structure. Blocking element 115 may be of any geometry within the tubular element. It may be added, placed or build up within the tubular structure. The example of 115 given in FIG. 1 is only meant for an illustrative purpose. In one preferred embodiment, the distance between any of the said elements was measured previously (for instance between 113 and 115). This previous measurement may therefore be combined with information extracted, for instance to calculate another distance (e.g. between 106 and 110).

In one embodiment, the exact dimensions of the tubular element or one of its subsections are calculated. This is achieved by using the monitoring option of the used device. It will be appreciated that other options to perform such a measurement are available such as tomography, geometrical measurements and so one. Independent of the device or method used, it is preferred that the used device has the ability to fill in the exact volume within the tubular element with composition. This is achieved by controlling the amount of injected composition, the shape of the tubular element and the position of the probe tip. In one preferred embodiment, the device is adjusted to fit into specific dimensions of a subsection of the cavity (such as illustrated in case of the blocking element 115 where the device fits into the space/element 115). A specific drill which carves a small step into the tubular element may be used for instance. Into this step the injection and illumination device may be placed, and if the distance between distal exit of the tubular element and step is known the amount to be injected composition can be precisely calculated. This circumvents any leakage of material, even if the distal exit of the tubular element is not blocked.

In some embodiments, the injection and/or illumination device can also be integrated into a drill or a file such as those usually used in dentistry. Hence, the injection and/or illumination system is thus used after or in parallel with the drilling device. The tubular body may be shaped according to the requirements of the operator and then filled with the composition using the injection, and also possibly illumination, device. Moreover, during drilling, the optical system may be used to guide the drill and estimate its position using the optical feedback.

Figure 2:
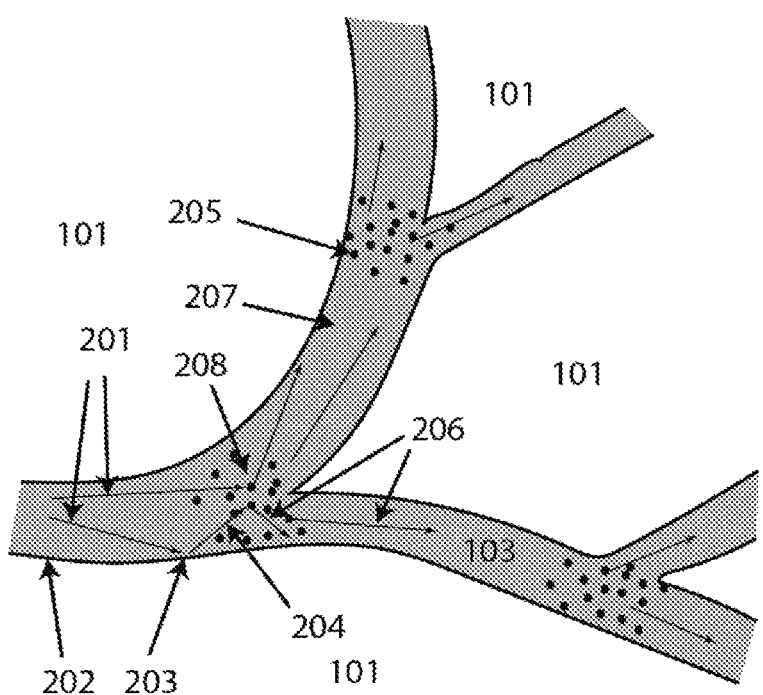
FIG. 2 depicts an illuminated composition with changing optical properties and experiment of light illumination within a tubular structure.

Light guiding within the tubular structure is achieved by different approaches such as scattering of particles distributed within the tubular structures, light reflection on the walls of the tubular structure or guiding within the material within the tubular structure such as within the composition. FIG. 2 illustrates another example of an illuminated tubular structure. Within the tubular structure 202, light 201 is propagated within the composition 103. It may be reflected by the wall of the tubular structure 203. This is achieved by using either the reflective properties of the tubular structure (if existent at the wavelength of 201) or by creating a difference between the refractive index of the composition 103 and the surrounding material 101. Total internal reflection may be used to propagate light. This requires that composition 103 contains or consists of a liquid with a higher refractive index (n) compared to the surrounding material 101. For instance water (n~1.333), fluoroquinolones (n~1.627), dimethyl sulfoxide (n~1.479), fat emulsion (n~1.36), liquid paraffin (n~1.48), paraldehyde (n~1.405), ethylene glycol (n~1.43), oil (n~1.47) or methylene iodine (1.737) are examples to reach high refractive indexes. The refractive indexes in brackets are approximations which vary depending on concentrations, illumination wavelength and purity of the material.

Furthermore, the invention also includes addition of heavy atoms to increase the refractive index locally. The heavy atoms used as radio opaque agents can also be used in turn as scattering elements in the present monitoring method. In one preferred embodiment, therefore, these heavy atoms are zirconium oxide, zinc oxide, calcium tungstate, barium sulfate, iodine, gold, gadolinium, platinum, silver or tantalum, as well as combinations thereof or derivate. Also other scattering materials such as those previously mentioned may be used. 204 thus represent light reflected at the position 203. In one embodiment, the light propagation within the tubular structure is achieved by adding scattering particles 205 to the composition 103. Almost any type of particle in the range between several nm and some mm induces a certain amount of scattering when irradiated with visible light. A person skilled in the art may refer to Rayleigh or Mie scattering of particles, elastic or inelastic scattering, scattering induced due to an electric field created within or/and around the particle and so on.

In a preferred embodiment the concentration of these scattering particles is varied within the composition 103. Typically, around bifurcations (208) more scattering is required, while in more cylindrically-shaped parts of the tubular structure 207 lower amounts of scattering particles are required. Depending on the concentration of the scatterers 205, the scattered light 206 will be transmitted rather into a radial or an axial direction within the tubular structure. Thus, an optimal overall light activation or light monitoring can be achieved. Moreover, the light can propagate into directions and to locations such as cracks, fissures or branches with an angle of 0° to 180° in respect to the main branch which could not be reached otherwise.

In one preferred embodiment, the tubular structure is filled stepwise with composition containing a high amount of scattering particles (e.g. close to bifurcations) and low amounts of scattering particles (e.g. when no bifurcations are present). Thus an illumination probe may be pulled back step by step. At each step composition is injected and light activated. The absolute value of the scattering coefficient of the composition will depend on the size of the tubular structure itself, thus depending on the size of the tubular structure the scattering coefficient of the composition may vary between 0.001 $cm^{-1}$ and 1000 $cm^{-1}$.

In one embodiment, the probe has mechanical properties which are adapted to give a haptic feedback. Typically, an elastic modulus of more than $10^6$ N/m$^2$, preferably more than $10^9$ N/m$^2$. This allows to photopolymerize a section of the tubular structure and then verify whether it has polymerized using the haptic feedback of the probe. In one preferred embodiment this mechanism is employed to build up a plug at the distal end of the tubular structure using photoactivation of the photosensitive material and then verify the solidity of the plug using the haptic feedback of the probe.

Figure 3:
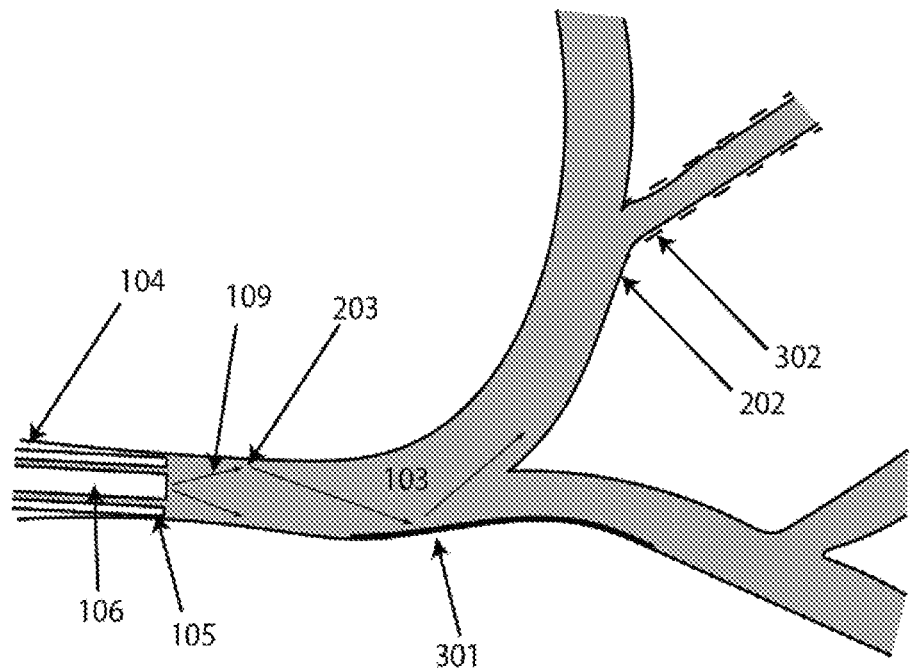
FIG. 3 depicts one embodiment of increased light guiding within the tubular structure by changing or/and machining the tubular structure

In one embodiment, a treatment is done to the tubular structure to enhance light propagation. FIG. 3 illustrates the application of a material to the wall of the tubular structure as well as geometrical changes of the tubular structure. A layer of material 301 may be placed on the inner wall of the tubular structure. This may be done by applying a coating, by irrigation or by flushing a material through the tubular structure which adheres to its walls. In one embodiment, the tubular structure 202 is treated mechanically or chemically to adapt its geometry and to increase light propagation. Thus, a new geometrical structure 302 is created. Examples for mechanical treatments are drilling (using a drill or a file), burning of material, laser ablation, ultrasound treatment, aspiration, wicking or any other removal method. Chemical removal of material may be achieved for instance by using acids or bases or any other liquid, gas or past-like material interacting with the wall of the tubular structure. In one preferred embodiment, sodium hypochlorite (NaOCl), sodium hypochlorite with surface modifiers, chlorhexidine gluconate, cetrimide, ethylenediaminetetraacetic acid (EDTA), framycetin sulfate, mixtures of citric acid, doxycycline and polysorbate 80 (detergent) (MTAD), calcium hydroxide, zinc chloride, stannous fluoride, chlorhexidine gluconate, hydrogen peroxide, bacteriostatic rising solution, doxycycline, polysorbate, camphorated monochlorophenol (CMCP), formocresol, cresatin, or calcium hydroxide, antimicrobal agents, carbamide peroxide, and propylene glycol, ethylene glycol-bis (b-aminoethyl ether-N,N,N',N'-tetraacetic acid), tannic acid, polyacrylic acid, bis-dequalinium-acetate, derivatives of oxine, doxycyline (e.g. 8-hydroxy-quinoline), tetracycline, non-ionic surfactant or similar compound or a mixture or aqueous solution thereof may be used to treat the tubular structure.

The pore size of the final, cross-linked composition can be tuned to foster or limit cell or bacteria migration. This is achieved by changing the molecular weight of a used polymer, by adding a composite material or by creating pores for instance by introducing a gas into the material before or during photopolymerization.

In one embodiment the distal tip of the delivery probe (105 & 106) or the region between distal and proximal end, contains an element to measure the electrical conductivity, resistance or impedance of the medium or surrounding body it is immerged into or put in contact with. This element may consist of several metal layers, coated or integrated electrodes, wires or any other geometrical element which is able to conduct electricity. There may be one or several of these elements. They may be placed on the wall of the probe, on its distal end or on its inside. In a preferred embodiment, the electrically conductive element will allow guiding or imaging of the probe, during placement, composition injection, optical monitoring or any other preformed action.

Figure 4:
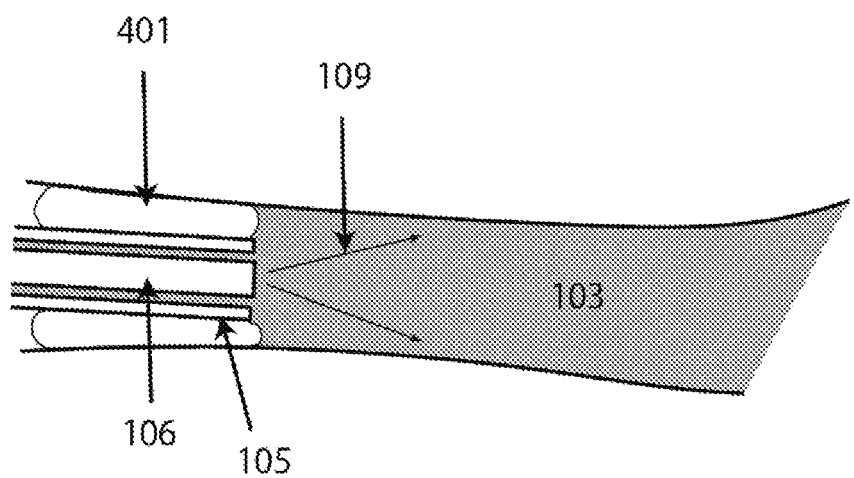
FIG. 4 depicts one embodiment of a blocking mechanism to stop the flow of the composition of the invention and/or other liquid or viscous material within a tubular structure.

In one embodiment a mechanism to temporally seal the space between probe and tubular element is described. As shown in FIG. 4, a cushion or balloon like element (401) is presented. It can be attached to the probe (105 & 106) or be placed within the tubular element before probe insertion into a tubular structure. It consists of a material which has the ability to exert a force onto the probe and onto the inner wall of the tubular element so to block any other material (e.g. blood or any other liquid, viscous material or gas) except the composition 103 to be placed in front of the probe. The element 401 may be for instance an inflatable balloon, expandable catheter, swellable material, shape memory polymer or alloy, an electrically actuated material as well as any other material or structure fulfilling the above conditions.

In one embodiment, a probe for the delivery of the composition comprises a pressurization mechanism such as commercially available syringe systems. In one preferred embodiment, the syringe is a screw syringe which allows for a controlled, step-wise delivery of the material in limited quantities such as drops and also easily allows increasing the pressure within the syringe.

In one preferred embodiment, the distal tip of the probe is a single use element including a connecting element to transmit light and a connecting element to deliver the composition. In one preferred embodiment, the tip of the light guiding element 106 only is disposable. In this preferred embodiment, it is cut (for instance using a fiber cutter) and thus a new tip of the light guiding element 106 is formed.

Figure 6:
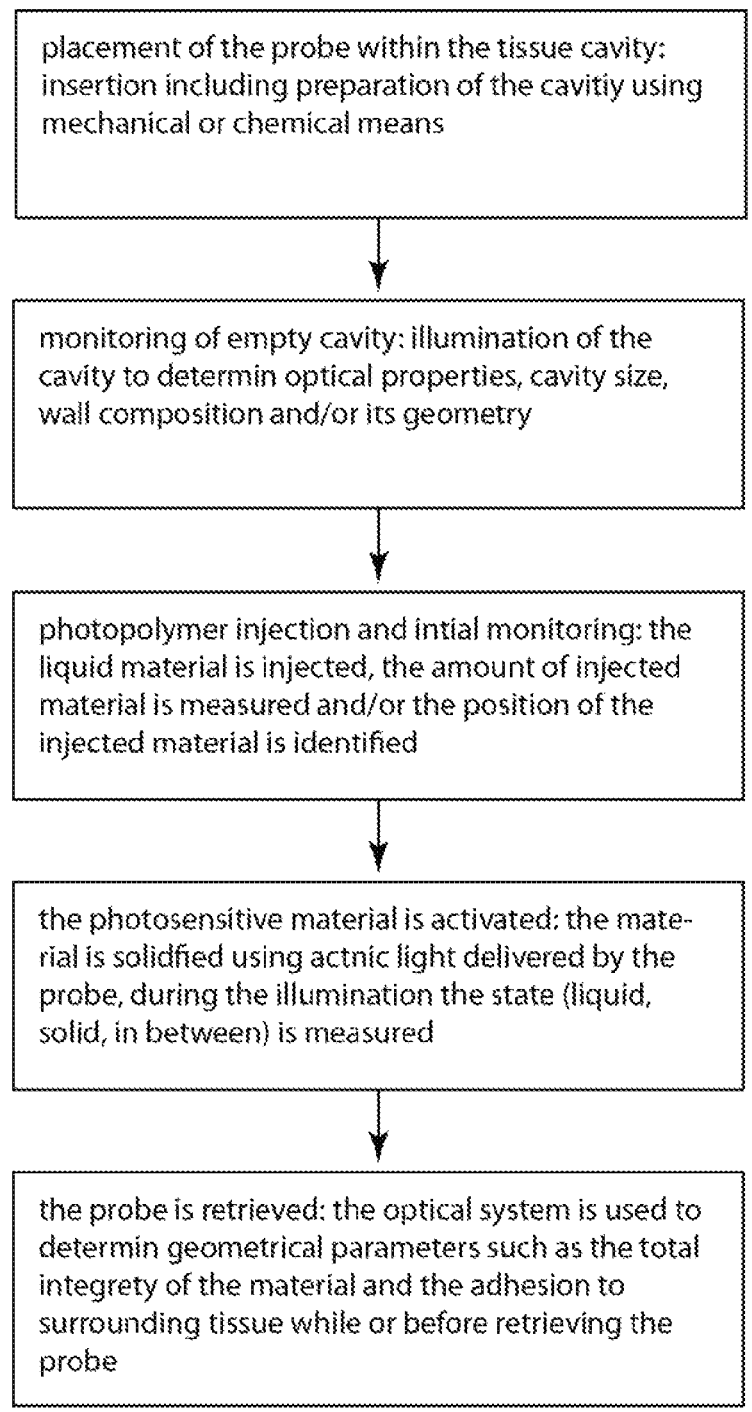
FIG. 6 depicts a flow diagram of the process for the use of the composition of the invention.

In one preferred embodiment the composition is injected droplet by droplet (or any other suitable quantity) and photoactivated sequentially. For instance, one drop may be placed at the distal end of the tubular structure to block its distal exit. Alternatively, the composition may be injected in a way to build a plug within the tubular element upon illumination. A general workflow of the process herein disclosed is shown in FIG. 6. The described method may consist of all or only one or several steps described in FIG. 6. In a preferred embodiment, any of the actions such as the preparation by drilling or filling are not necessary. This is due to the high viscosity of the injected composition which is able to flow into interstices which usually would not be accessible by a state of the art system.

Figure 7:
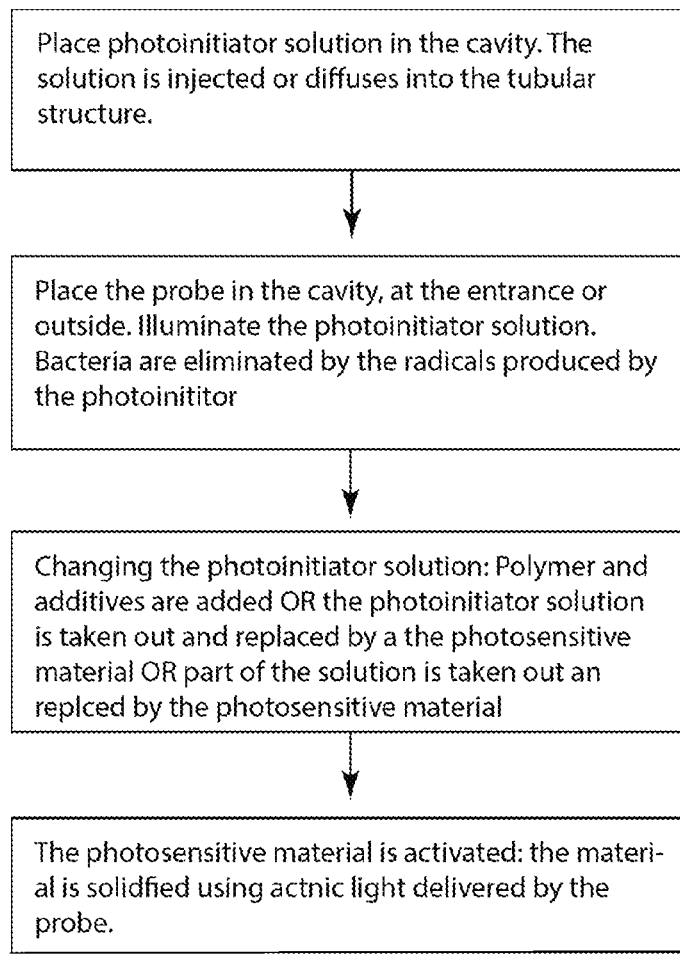
FIG. 7 depicts a flow diagram of another embodiment of the process for the use of the composition of the invention, comprising a first disinfection step.

In one embodiment, a photoinitiator solution (solvent+photoinitiator) is placed in the cavity first. The probe for photoactivation is thus used for disinfection of the tubular structure as presented in the non-limiting embodiment shown in FIG. 7. The photoinitiator solution is placed first within the cavity. Upon illumination with the probe, radicals are produced which will then disinfect the cavity. The illumination duration may vary between 1 and 1000 seconds, preferably between 20 and 200 seconds. Any of the photoinitiators and solvent mentioned previously may be used including additives to further enhance the diffusion of the material into the tubular structure or to improve the antibacterial effect. After photoactivation of the photoinitiator solution, the photosensitive material is placed into the cavity. This may be done by replacing the photoinitiator solution or by partially replacing the photoinitiator solution. In a preferred embodiment, part of the photoinitiator solution is kept in the tubular structure and the photosensitive material is added. Thus, part of reacted and unreacted photoinitiator from the photosensitive solution may remain inside the cavity. Following the placement of the photosensitive material, it is activated using the probe. Remaining photoinitiator solution is activated, too.

EXAMPLES

In an exemplary experimental setting, different compositions, comprising different amounts and combinations of radio opaque agents, were tested. Samples were prepared in 2 and 4 mm deep molds and illuminated at 365 nm (around 1.25 mW/cm$^2$) from top during a fixed time of 5 minutes. The solvent (i.e., the carrier) used to dilute metal particles of radio opaque materials was water, or when a radiopaque material was available as a liquid, aqueous contrast agent, the agent itself was the solvent. The metal particles, formulations thereof or derivatives thereof were suspended in the liquid solution, in the amounts shown in Table 1 above. 10 g every 100 ml of composition of Polyethylene glycol dimethacrylate was used as polymeric cross-linkable material. In summary, Table 1 shows that low amounts of metal-based additives such as those used in bone cements (8-10%) are not sufficient to reach radiopaque densities of more than 1.5 mmAl/mm or were even too low to be detected ("Out of range") by the micro CT scanner (used voltage and current: 100 kV and 100 uA). In many cases, the light is either absorbed by the radio opaque agent during photopolymerization ("no photopolymerization"), or the radiopaque particles agglomerate, which results in a high heterogeneity of the samples ("low homogeneity"). A combination of a liquid contrast agent and dispersed particles was able to reach radiopacity values above 3 or 6 mmAl/mm while still being photopolymerizable. A formulation comprising a combination of Iodine and Calcium Tungstate was able to reach high radiopacity (>6 mmAl/mm), low viscosity (injectable through a 30 gauge needle) and a sufficient degree of photopolymerization, wherein for sufficient degree of polymerization it is meant that the sample had solidified and was not liquid, viscous or semi-solid anymore.

Figure 5:
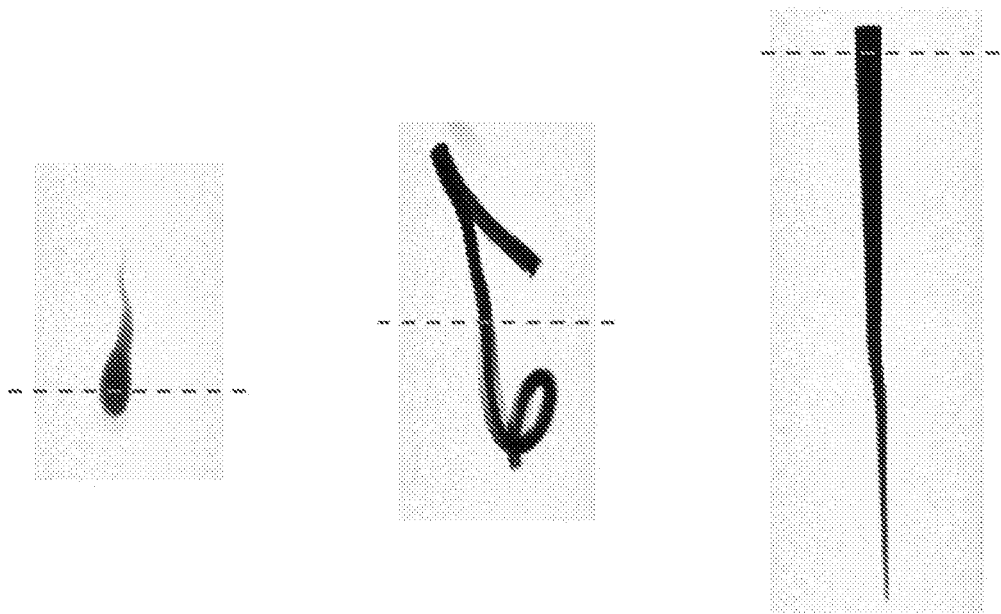
FIG. 5 shows an X-ray image of a hydrogel injected within a rubber tube vs. other sealers and Glutta Percha.

When compared to commercially available sealer and Gutta Percha, the proposed formulation (15 & 16 in Table 1) shows higher radiopaque densities. FIG. 5 shows a sample of a commercially available sealer (TotalFill®, BC Sealer™, on the left) with a measured radiopaque density of 2 mmAl, one preferred embodiment of the composition of the invention (middle; formulation 16 in Table 1) with a density of 6 mmAl/mm and commercially available Glutta Percha (right) with a measured opacity of 2.4 mmAl/mm. The dotted line indicates where the measurement was taken. The highest (darkest) grey value on the line was compared to an aluminum wedge with a given thickness. Further information on the measurement method may be found in ISO standard 13116:2014. The sample in the middle was photopolymerized within 2 minutes within a 3 cm long tubular element with an internal diameter of 1 mm.

The invention claimed is:

1. A liquid or semi-solid composition for use as a filling agent for hollow structures, the composition comprising: a liquid carrier, a cross-linkable polymeric material, a cross-linking agent, and a radio opaque agent, the radio opaque agent comprising a liquid agent and dispersed particles, the liquid carrier and the liquid agent being different materials, and the liquid carrier being an aqueous solution or a nonpolar solution,
  wherein the composition has the radio opaque agent as a percent by weight component such that the composition has
  i) an opaque density equivalent to at least 3 mmAl/mm, and
  ii) a viscosity between $2\times10^{-4}$ and $1\times10^3$ Pa*s.

2. The composition of claim 1, wherein the cross-linkable polymeric material has an optical density resulting in an absorption coefficient of less than 1000 cm$^{-1}$ at a wavelength between 350 and 600 nm.

3. The composition of claim 1, wherein the cross-linkable material is present in an amount comprised between about 0.5 g and about 40 g per 100 ml of the composition.

4. The composition of claim 1, wherein the cross-linkable material comprises a thermoset material or a hydrogel material.

5. The composition of claim 1, wherein the crosslinking agent includes a photoinitiator.

6. The composition of claim 5, wherein the photoinitiator is present in an amount of at least about 0.001% by weight of the composition, and in an amount of less than about 15% by weight of the composition.

7. The composition of claim 5, further comprising:
  a co-initiator which is present in a molar ratio with respect to a photoinitiator or co-initiator comprised between about 100:1 and about 1:100.

8. The composition of claim 1, wherein the radio opaque agent comprises one or several types of radiopaque atoms or molecules thereof.

9. The composition of claim 1, wherein the radio opaque agent is present in an amount comprised between about 1 g to about 200 g per 100 ml the composition.

10. The composition of claim 1, wherein the radio opaque agent comprises a mixture of Iodine or a Iodine-based material and a metal or a metal-based material, salt thereof and/or oxide thereof.

11. The composition of claim 10, wherein the ratio between the Iodine-based material and other radio opaque materials is comprised between about 2:1 to 1:2 by weight.

12. The composition of claim 1, wherein the hollow structures are tubular structures and have a diameter between 10 μm and 20 mm.

13. The composition of claim 1, wherein the tubular hollow structures are dental root canals and accessory canals, pulp chamber, blood vessels, lymphatic vessels, bronchi and bronchioles and artificially-created tubular structures.

14. The composition of claim 1, wherein the cross-linkable polymeric material comprises a hydrophilic polymeric material having a molecular weight comprised between 700 Da and 25 kDa, providing an osmotic pressure against a wall of a hollow structure upon injection therein between 50 kPa and 10 MPa.

15. The composition of claim 1, wherein the radio opaque agent comprises a metal or a metal-based material selected from a list comprising barium sulphate, zirconium oxide, zinc oxide, calcium tungstate, gold, gadolinium, silver, platinum, tantalum, salts thereof and/or oxides thereof.

16. The composition of claim 1, wherein the cross-linkable polymeric material is biodegradable.

17. The composition of claim 1, wherein the liquid agent of the radio opaque agent is iodine, and wherein the dispersed particles include calcium tungstate.

18. A composition, comprising:
  a liquid carrier comprising from 0.5 to 90 g per 100 ml of the composition, the liquid carrier being an aqueous solution or a nonpolar solution;
  a cross-linkable polymeric material comprising from 0.5 g to 40 g per 100 ml of the composition;
  a cross-linking agent comprising at least 0.001 percent by weight of the composition; and
  a radio opaque agent, the radio opaque agent comprising from 1 g to 200 g per 100 ml of the composition.

19. The composition of claim 18, further comprising:
  a photoinitiator comprising a molar weight ratio of the composition from 100:1 to 1:100, wherein the radio opaque agent comprises a liquid agent and dispersed particles.

* * * * *